United States Patent [19]
Southworth

[11] Patent Number: 5,935,084
[45] Date of Patent: Aug. 10, 1999

[54] INFLATABLE PRESSURE INDICATOR

[75] Inventor: Carleton B. Southworth, Lakeville, Mass.

[73] Assignee: Johnson & Johnson Professional, Inc., Raynham, Mass.

[21] Appl. No.: 08/940,667

[22] Filed: Sep. 30, 1997

[51] Int. Cl.⁶ .................................................. A61B 5/00
[52] U.S. Cl. .......................................................... 600/561
[58] Field of Search ..................... 600/561, 587, 600/593; 73/729.1, 729.2; 33/572

[56] References Cited

U.S. PATENT DOCUMENTS

| | | | |
|---|---|---|---|
| 3,625,199 | 12/1971 | Summers | 128/2 R |
| 4,114,458 | 9/1978 | Alinari | 73/729.1 |
| 4,206,762 | 6/1980 | Cosman | 600/561 |
| 4,231,376 | 11/1980 | Lyon et al. | 128/748 |
| 4,481,952 | 11/1984 | Pawelec | 600/593 |
| 4,589,287 | 5/1986 | Dickens | 73/727 |
| 4,627,443 | 12/1986 | Chubbuck et al. | 128/748 |
| 4,723,556 | 2/1988 | Sussman | 128/748 |
| 5,257,630 | 11/1993 | Broitman et al. | 128/675 |
| 5,325,865 | 7/1994 | Beckman et al. | 128/748 |

*Primary Examiner*—Max Hindenburg
*Attorney, Agent, or Firm*—Nutter, McClennen & Fish, LLP

[57] ABSTRACT

An implantable pressure measurement device is effective to measure a physiological pressure, which pressure can be ascertained by external imaging of the device. In one embodiment, a predetermined amount of a fluid is sealed in a flexible member which is disposed in a housing. A position indicating member is coupled to one end of the flexible member. The fluid expands and contracts the flexible member in response to external pressure changes. A physiological pressure is determined by ascertaining the relative location of the position indicating member on the housing. An external imaging system is used to view scale markings located on the position indicating member and the housing. In another embodiment, an elongate member is axially movable within a housing. A sealing member seals an amount of air in a portion of the housing and is sealably engaged with one end of the elongate member. A physiological pressure is determined using an imaging system to determine the position of the elongate member.

12 Claims, 6 Drawing Sheets

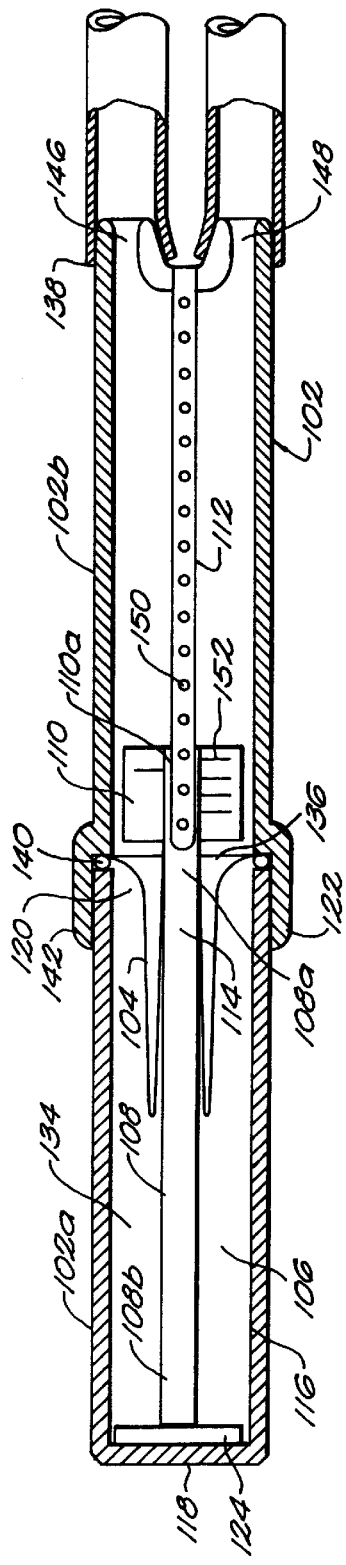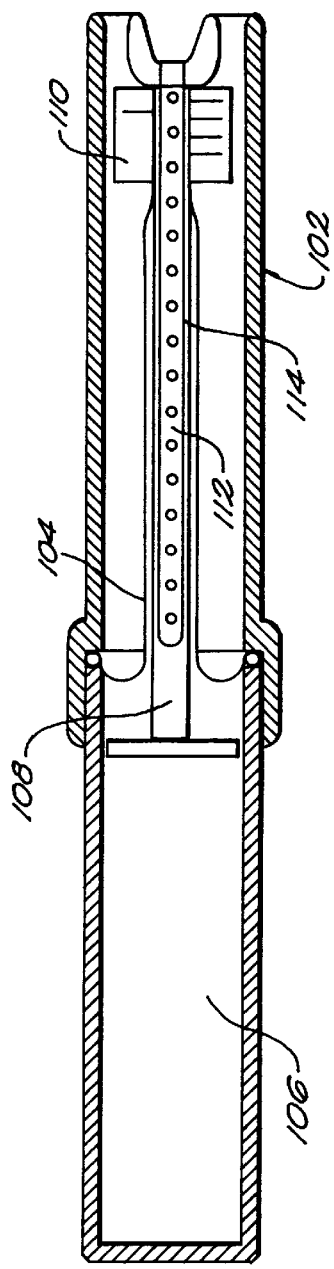

INFLATABLE PRESSURE INDICATOR

CROSS REFERENCE TO RELATED APPLICATION

Not Applicable.

STATEMENT REGARDING FEDERALLY SPONSORED RESEARCH

Not Applicable.

BACKGROUND OF THE INVENTION

The present invention relates to pressure measurement devices, and more particularly to an implantable pressure measurement device that provides physiological pressure information via an external imaging system.

Pressure measurement devices of various types are used to measure a physiological pressure in different areas within the body of a patient. One application of such devices is in the treatment of hydrocephalus, a condition where cerebrospinal fluid (CSF) collects in is the ventricles of the brain of a patient. CSF is produced by the choroid plexis in the ventricle system and is normally absorbed by the venous system. However, if an unbalance between CSF production and the absorption of the CSF occurs, the volume of CSF increases thereby elevating the intracranial pressure. This excess CSF can result in abnormally high epidural and intradural pressures. Left untreated, hydrocephalus can result in serious medical conditions, including subdural hematoma, compression of the brain tissue and impaired blood flow that consequently can impair cognitive and motor function.

To determine the intracranial pressure, a pressure measurement device can be inserted into the patient to measure the pressure. One such device is a catheter having a sensor for in vivo measurement of intracranial pressure in which one end of the catheter is disposed in the ventricular region of the brain and the other end exits the cranial region for coupling to a monitor. The measurement of intracranial pressure with such a device is an invasive procedure having certain concomitant risks, such as infection and human error. Thus, monitoring intracranial pressure with this type of device is best suited for short term use only.

Once it is determined that intracranial pressure is above acceptable levels, the pressure should be relieved. Various drainage catheters or shunt systems have been developed to remove the excess CSF and to discharge the fluid to another part of the body, such as the peritoneal region. By draining the excess fluid, the elevated intracranial pressure is reduced.

Generally, CSF shunt systems designed for long term use are implantable within the patient. Such CSF shunt systems include a valve mechanism for controlling or regulating the flow rate of fluid through the system. An illustrative shunt system includes a valve mechanism in fluid communication with a brain ventricular catheter. The ventricular catheter is inserted into a ventricle of the brain and a peritoneal catheter is inserted into the peritoneal region for discharge of the fluid. While such implanted catheters can drain excess CSF if working properly, intracranial pressure information is not readily available without an invasive surgical procedure.

Shunt systems typically permit fluid flow only when the fluid pressure reaches a threshold pressure for the shunt valve. The threshold pressure that allows fluid flow through a shunt system must sometimes be adjusted. For example, a surgeon may initially select a relatively low threshold pressure to trigger fluid flow. Over time, the initial threshold pressure may not be ideal. For example, it could lead to excess fluid flow, creating an undesirable overdrainage condition caused by too much fluid being drained from the ventricle. A CSF overdrainage condition can result in a dangerously low intracranial pressure. Such a situation may give rise to a need to increase the threshold pressure to afford a fluid flow rate that is balanced to avoid both excessive intracranial pressure and overdrainage conditions.

Some shunt systems can become clogged or may malfunction mechanically. When a patient exhibits symptoms that could be related to shunt malfunction it is often desirable to evaluate whether the shunt system is functioning properly and/or to evaluate intracranial pressure directly. If the threshold pressure is set too high, or if the valve is occluded, excessive CSF will not be discharged via the shunt system to relieve intracranial pressure. If the threshold pressure of the valve mechanism is set too low, or if the valve is stuck open, a CSF overdrainage condition can occur. Shunt system operation can be monitored by observing the pressure on fluid in the shunt system. However, as discussed above, monitoring the pressure of an implanted shunt system can require an undesirable invasive surgical procedure.

An implantable pressure measurement device is needed that provides physiological pressure information, without invasive surgical procedures. It would also be desirable to monitor the operation of certain implanted devices, such as fluid shunt systems.

SUMMARY OF THE INVENTION

The present invention provides a pressure measurement device adapted for surgical implantation in the body of a patient that is useful for determining physiological pressures. The device can be adapted for implantation by itself, or for coupling to an implantable shunt system. Although the device is primarily described and illustrated in conjunction with measuring intracranial pressure, it is understood that it can be used for measuring other physiological pressures as well, such as blood pressure in the heart or pressure in the gastrointestinal tract.

In one embodiment, a pressure measurement device includes a housing having a passageway leading to a chamber with at least one scale marking disposed on the passageway of the housing. A flexible member that contains an amount of fluid is disposed within and can axially expand and contract within the chamber. A position indicating member having at least one position marking extends from the flexible member and is movable in the passageway. The relative position of the position indicating member with respect to the scale marking is indicative of the volume of the fluid in the flexible member. Since the volume of the fluid is a function of pressure and temperature, the physiological pressure can be determined based on the measured volume.

As the pressure external to the device changes, the fluid in the flexible member expands or contracts to equalize the pressure on the fluid in the flexible member and the external pressure. An increase in such external pressure results in compression of the fluid in the flexible member. Conversely, as the external pressure decreases, the fluid contained by the flexible member expands. The expansion and contraction of the fluid moves the flexible member, thereby altering the location of the position indicating member in the passageway of the housing. As the position indicating member moves, the position marking migrates with respect to the scale marking on the housing, and the location of the position marking on the scale can be observed with an external imaging system. By determining the location of the position indicating member in relation to the scale marking, the volume of the fluid in the flexible member and the pressure external to the device can be ascertained. The differential between the pressure external to the device and ambient pressure represents the physiological pressure at the site of implantation.

In another embodiment, a pressure measurement device includes a housing having a first end, a second end and an intermediate portion therebetween. The housing defines inner walls and an outer surface with at least one passageway formed through the housing. An elongate member, including a first end and a second end with a bore extending from the first end thereof, is axially movable in the housing between a first position and a second position. A position indicating member is preferably secured to the elongate member proximate the first end thereof with at least one position marking located on the position indicating member. A flexible sealing member is disposed in the housing at the intermediate portion and divides the housing into a first portion adjacent the first end and a second portion adjacent the second end. The sealing member cooperates with the housing and the elongate member to trap an amount of a fluid in the first portion of the housing. A rod extends from the second end of the housing and has at least one scale marking located thereon. The rod is insertable in the bore of the elongate member as the elongate member moves in the housing.

A pressure external to the device is in communication with the sealing member via the passageway in the housing to equalize the pressure of the fluid external to the device and the fluid in the first portion of the housing. The fluid in the first portion of the housing responds to changes in the external pressure by expanding or contracting. Such expansion or contraction causes the elongate member to move within the housing. As the elongate member moves, the position marking shifts with respect to the scale marking on the rod. The scale marking and the position marking are observable through an external imaging system to determine the location of the position marking on the elongate member with respect to the scale marking on the rod. The location of the position marking provides an indication of the volume of the fluid in the first housing, from which the pressure external to the device is determined. The physiological pressure at the site of implementation is determined based on the differential between the external pressure and the ambient pressure.

BRIEF DESCRIPTION OF THE DRAWINGS

The invention will be more fully understood from the following detailed description taken in conjunction with the accompanying drawings, in which:

FIG. 9 is a cross sectional view of another embodiment of a pressure indicator in accordance with the present invention shown in a first position;

FIG. 10 is a cross sectional view of the pressure indicator of FIG. 9 shown in a second position;

DETAILED DESCRIPTION OF THE INVENTION

Figure 1:
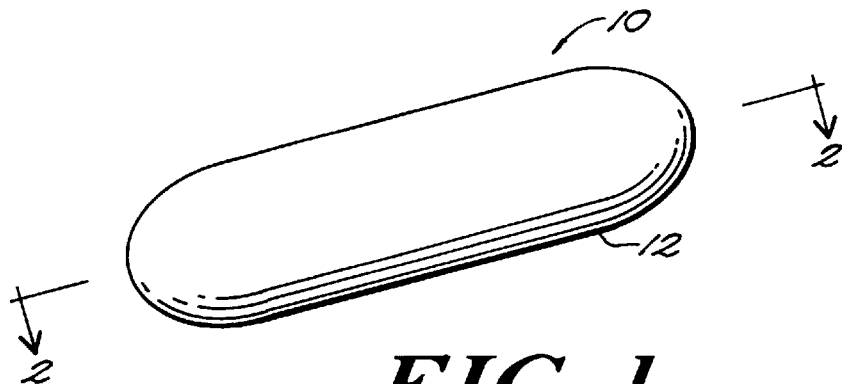
FIG. 1 is a perspective view of a pressure indicator in accordance with the present invention, including an optional covering member.
Figure 2:
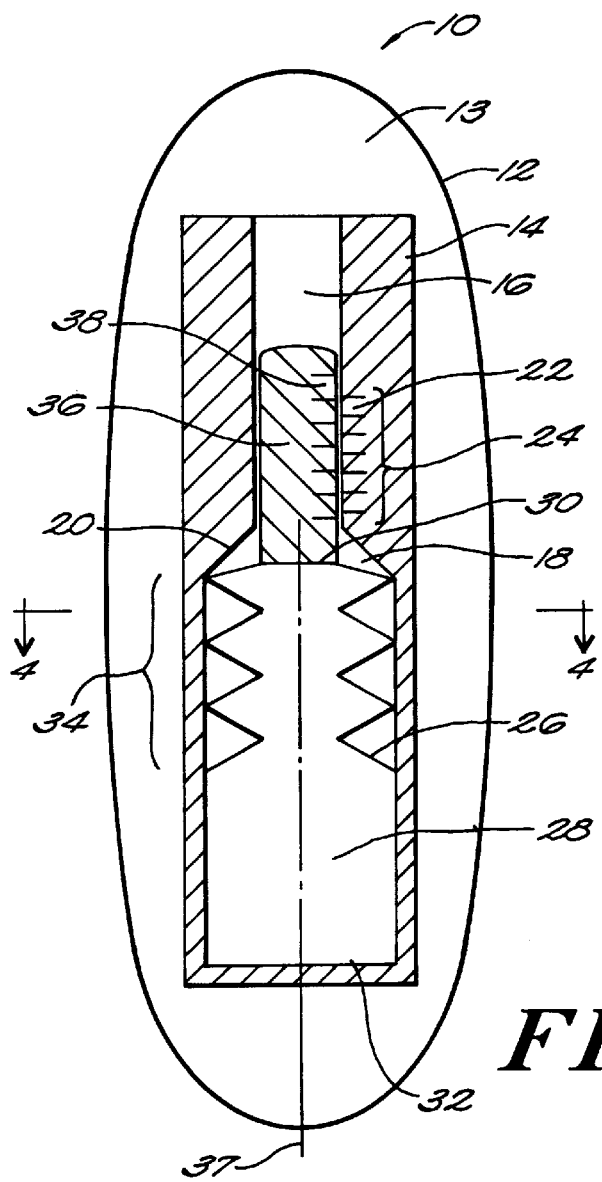
FIG. 2 is a cross sectional view of the pressure indicator of FIG. 1 along lines 2—2.
Figure 3:
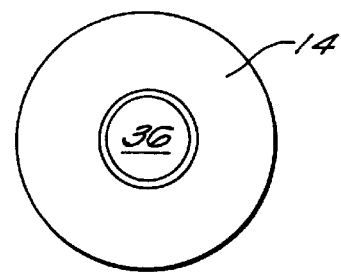
FIG. 3 is an end view of the pressure of the pressure indicator of FIG. 1 shown without the covering member.
Figure 4:
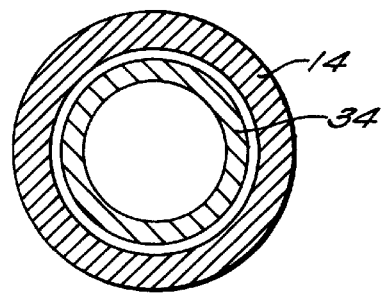
FIG. 4 is a cross sectional view of the pressure indicator of FIG. 2 along lines 4—4 shown without the covering member.

The present invention provides an implantable pressure measurement device that renders physiological pressure information without invasive surgical procedures. In one application, the device is implantable as a stand-alone unit. In another application, the device is coupled to an implantable shunt system to monitor pressure of fluid in a shunt system. The device can also be coupled to an external drainage system. It is understood that the device can be used in other applications that will be readily apparent to one of ordinary skill in the art, such as monitoring blood pressure and pressure within the gastrointestinal tract. Furthermore, the drawings are not to scale and are intended to facilitate an understanding of the invention. Accordingly, the invention is not to be limited to the particular applications and embodiments shown and described herein.

FIGS. 1–4 show a pressure measurement device 10 adapted for stand-alone implantation at a location in the body of a patient, such as in the cranium. The device can be tethered by a flexible chord made of silicone or other biocompatible material that is sutured to a burr hole or craniotomy site. An optional covering 12 isolates the device from bodily fluids and the like to prevent biological substances and deposits from interfering with the performance of the device. The covering 12 can contain a fluid 13 which can be a biocompatible gas or liquid, such as air.

The pressure measurement device 10 includes a housing 14 having a passageway or neck 16 extending into a chamber 18. The neck 16 can include a tapered portion 20 that widens into the chamber 18. At least one scale marking 22 is located on the neck 16 of the housing to form a portion of a scale 24, which is discussed below.

A flexible member 26, which contains a predetermined amount of a fluid 28, is disposed in the chamber 18. The flexible member includes a first end 30 and a second end 32 with a bellows portion 34 therebetween. The bellows portion 34 readily expands and contracts along a longitudinal axis 37 of the chamber 18. The second end 32 of the flexible member can be secured to the chamber 18 to allow maximum extension of the flexible member before the first end 30 abuts the tapered portion 20 of the neck.

The flexible member 26 generally conforms to the contour of the chamber 18. In an exemplary embodiment, the chamber 18 and the flexible member 26 are generally concentric cylinders. The flexible member 26 and the bellows portion 34 have a diameter which is slightly smaller than a diameter of the chamber 18. Thus, the flexible member 26 is contained within the chamber 18, but the chamber does not impede axial movement of the bellows portion 34.

The fluid 28 in the flexible member can be air, nitrogen, oxygen, or another suitable, preferably non-toxic, gas or fluid. A preferred fluid is air. The fluid 28 can be placed in the flexible member at a known pressure and temperature. In an exemplary embodiment, the fluid 28 in the flexible member is initially at atmospheric pressure at the site of assembly and typical body temperature (i.e., 37 degrees C.). In another embodiment, the air is sealed in the flexible member 26 at a pressure of 10400 mm $H_2O$ at typical body temperature.

A position indicating member 36 extends from the first end 30 of the flexible member into the housing neck 16. The position indicating member 36 can be integral with the flexible member 26 or affixed thereto. At least one position marking 38 is disposed on or in the position indicating member 36. The position marking 38 forms a portion of the scale 24, which, as described below, indicates the relative position of the position indicating member 36 with respect to the housing 14.

The scale and position markings 22,38 can be formed from various materials that are discernible, i.e., at least partially opaque, to an imaging system, such as an X-ray, fluoroscope, ultrasound, computed axial tomography (CAT) scan, magnetic resonance imaging (MRI) system, position emission (PET) or other such system. Exemplary materials for the scale and position markings 22,38 include radiopaque metals such as titanium, titanium alloys, stainless steel, boron, tantalum, cobalt chrome alloys, gadolinium, barium, and radiopaque materials such as barium sulfate, doped methylmethacrylate, zirconium dioxide, alumina, hydroxyapatite, and processed bone. It is understood that the material to be used must be compatible with a desired imaging system. In an exemplary embodiment, tantalum is used for markings that are able to be viewed with an X-ray system.

The scale and position markings can each be identical in dimension and composition, or they can be unique. The markings can sequentially change in dimension or composition in a predetermined pattern that is readily apparent in a corresponding imaging system. For example, the markings can sequentially vary in opacity to appear progressively darker when displayed on an imaging system. In an illustrative embodiment, the position markings 38 include four lines spaced at about 1.2 millimeters and the scale markings 22 include 18 lines equally spaced at 1.0 millimeter to form a Vernier scale.

The dimensions of the various device components can vary. It is important that the relative dimensions of the components be such that the flexible member is axially movable in the chamber with minimal friction or interference. The chamber should provide sufficient axial extension to allow movement of the flexible member for an expected pressure range of the device. The dimensions of these components will vary depending upon the requirements of a given application and the anticipated site of implantation. One of ordinary skill in the art can readily determine the appropriate relative dimensions of the device components.

Generally, the overall length of the housing 14 can be from about 10 millimeters to about 60 millimeters, and more preferably from about 20 millimeters to about 35 millimeters. The housing width can range from about 2 millimeters to about 6 millimeters, and preferably about 4 millimeters.

The chamber 18 can have a length from about 10.0 millimeters to about 60.0 millimeters and a width of about 1.8 millimeters to about 5.0 millimeters. In one embodiment, the length of the chamber 18 is about 34.0 millimeters and the width is about 4.0 millimeters.

The device 10 provides non-invasive pressure measurements based on the equalization of the pressure on the fluid 28 trapped within the flexible member and a pressure external to the device. The external pressure is communicated to the flexible member 26 via the passageway 16 in the housing, thus influencing the location of the position indicating member 36. The relative location of the position indicating member 36 is ascertained through the use of an external imaging system (not shown) to determine the location of the position marking 38 as compared to the scale marking 22 on the housing. The position of the position indicating member 36 indicates the volume of the fluid 28 in the first housing. The external pressure is determined from the volume of the fluid as described below.

As the external pressure increases, the bellows portion 34 of the flexible member 26 contracts as the fluid is compressed causing the position marking 38 to move in one direction with respect to the scale marking 22. As the external pressure decreases, the bellows 34 of the flexible member 26 extends to move the position marking 38 in the opposite direction as the fluid expands. The location of the position marking 38 indicates the differential between the initial volume of fluid 28 trapped at manufacture at an initial pressure and the volume of the fluid 28 in the presence of an external pressure. Thus, the device measures fluid volume directly and pressure indirectly.

The fluid 28 volume reading is used in conjunction with pressure information to determine a pressure proximate the site of implantation. The initial pressure on the fluid 28 in the flexible member 26 and initial scale reading are known at the time of assembly. This information is used to determine a relationship between the scale reading and the external pressure. For example, from an initial (assembly) pressure of about 10333 mm $H_2O$ and initial location of the position indicating member 36 with respect to the scale, the pressure/scale(volume) relationship can be determined. That is, for each location of the position indicating member 36 with respect to the scale, the corresponding external pressure is known.

The ambient or atmospheric pressure is established at the time and location of device measurements using conventional methods and/or devices. A reading of the device provides the volume of the fluid 28 which corresponds to an external pressure. The ambient pressure is subtracted from the external pressure to obtain the pressure differential, i.e., the pressure at the site of implantation. For example, where the device provides a fluid volume reading corresponding to an external pressure of about 10433 mm $H_2O$ at an ambient pressure of about 10400 mm $H_2O$, the pressure differential at the site of implantation (i.e., intracranial pressure) is about 33 mm $H_2O$. Thus, a physiological pressure, i.e., the pressure differential, is determined by reading the scale to determine the external pressure and subtracting ambient pressure from the external pressure.

If a patient has a body temperature other than normal, this temperature differential can reduce the accuracy of a device measurement. For example, where the fluid in the flexible member is a gas, such as air, an increase in temperature of the air results in a proportional increase in the volume of the air. The increased volume of the air thereby affects the scale reading of the device with respect to determining pressure. Similarly, for a patient having a body temperature less than typical body temperature, a proportional decrease in air volume occurs. Temperature compensation for the device is readily determined from the initial pressure, temperature, and volume, scale reading, body temperature, and the constant of expansion for the gas in the flexible member.

The pressure measurement device components can be made from a variety of bioimplantable materials having suitable properties for the particular component. The housing 14 preferably is formed from a material that is impermeable to bodily fluids and the like, and is dimensionally stable over a range of expected operating pressures and temperatures. Exemplary materials include metals such as titanium, titanium alloys, stainless steel, and cobalt-chromium alloys, and polymers such as polyethylene, ultra-high molecular weight polyethylene, and polyethersulfone. A preferred material is polyethersulfone.

The flexible member 26 preferably is formed from a suitably flexible material that can also be elastic. Exemplary materials include titanium and mylar. Silicone is a preferred material.

The position indicating member 36 preferably is formed from a rigid bioimplantable material such as a high durometer silicone or titanium. The material can be the same as or different from that of the flexible member 26. A preferred material for the position indicating member is silicone.

The outer covering 12 can be formed from a bioimplantable elastomer such as silicone, polyurethane, polyethylene or metal foil. In an exemplary embodiment, the outer covering is formed from silicone.

Figure 5:
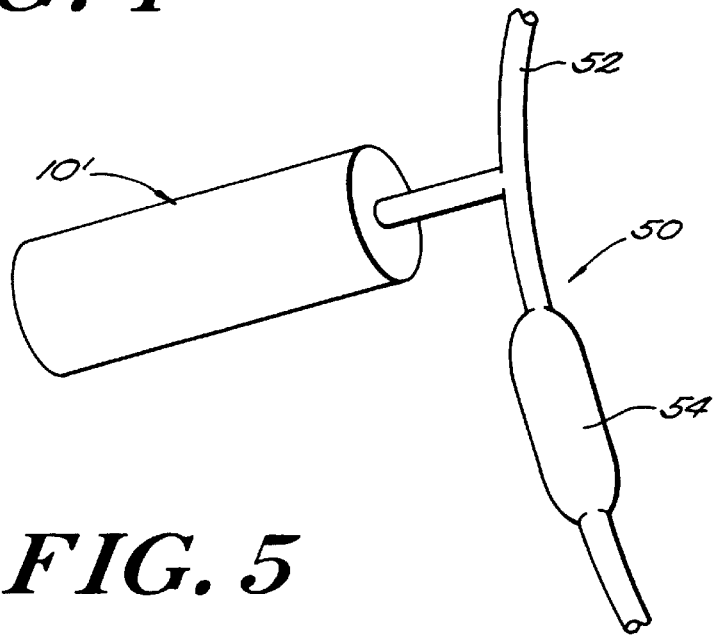
FIG. 5 is a perspective view of an alternative embodiment of the pressure indicator of FIG. 1.
Figure 6:
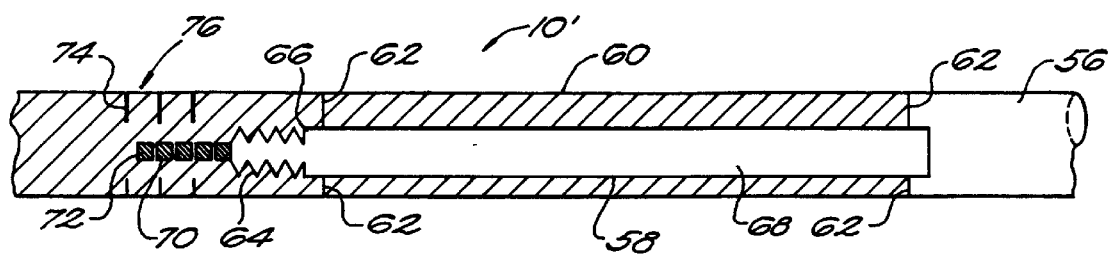
FIG. 6 is a cross sectional view of another embodiment of the pressure indicator of FIG. 1.

FIGS. 5–6 show another embodiment of a pressure measurement device 10' coupled to an implantable CSF shunt system 50. The device 10' is coupled to the shunt system 50 fluid path via surgical tubing 52. The device 10' can monitor operation of a valve mechanism 54 in the shunt system by monitoring a pressure required for CSF to pass through the shunt system. The CSF pressure should be within desired levels to allow drainage of excess CSF while avoiding overdrainage conditions.

As shown in FIG. 6, the pressure measurement device 10' has a shunt end 56 adapted for coupling with the shunt system 50. The device 10' has an inner tube 58 axially secured in an outer tube 60 by spokes 62. A flexible member 64 extends from a first end 66 of the inner tube 58 with an amount of a fluid 68 trapped within the inner tube 58 and the flexible member 64. A position indicating member 70 is coupled to the flexible member 64 and axially expands and contracts as the fluid 68 volume changes. Position markings 72 are located on the position indicating member 70 and scale markings 74 are disposed about a circumference of the outer tube 60 to form a Vernier scale 76. An external imaging system is used to view the scale 76 and determine the location of the position indicating member 70 in the outer tube 60, and ultimately a physiological pressure.

Figure 7:
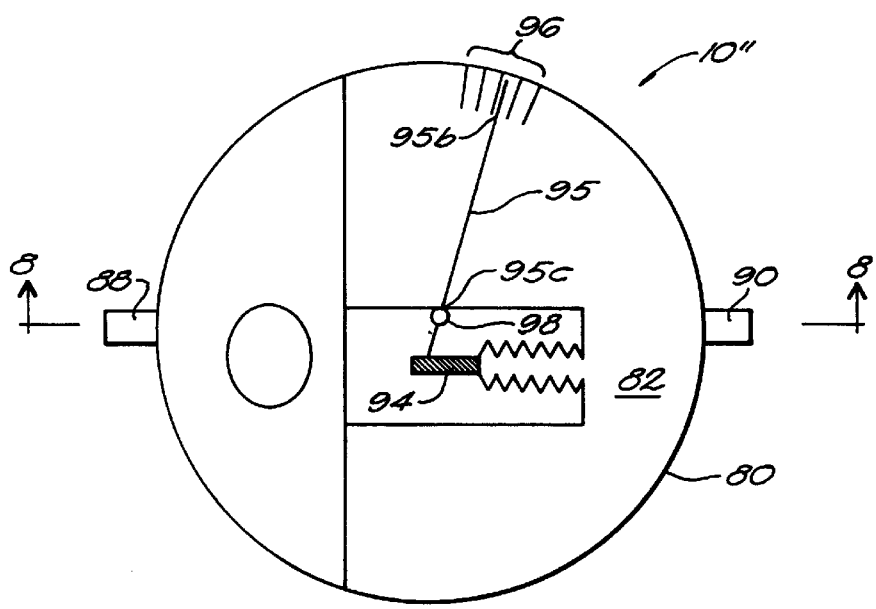
FIG. 7 is a top view of a further embodiment of the pressure indicator of FIG. 1 shown without a portion of a housing.
Figure 8:
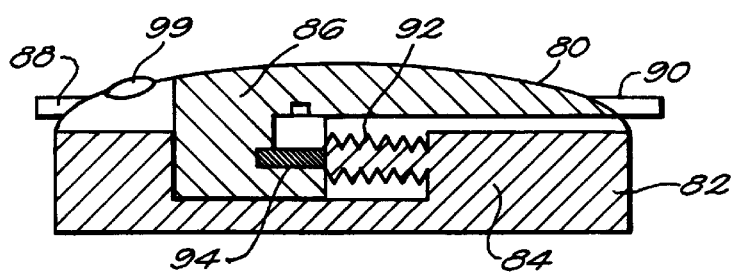
FIG. 8 is a cross sectional view of the pressure indicator of FIG. 7 along lines 8—8.
Figure 11:
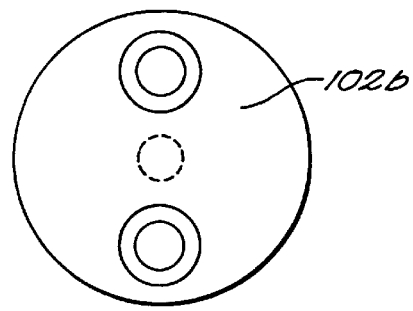
FIG. 11 is an end view of the pressure indicator of FIG. 9.

In FIGS. 7–8, a pressure measurement device 10" is adapted for placement within a CSF fluid reservoir which forms a portion of a CSF shunt system (not shown). The device 10" has a rigid housing 80 with a first chamber 82 having an amount of a fluid 84 trapped therein, and a second chamber 86 having a first opening 88 and a second opening 90 to allow the passage of CSF. A flexible member 92 forms a portion of the first chamber 82 and expands and contracts in response to changes in volume of the fluid 84. Extending from an end of the flexible member 92 is a position indicating member 94. A needle 95 has a first end 95a coupled to the position indicating member 94 and a second end 95b proximate a series of scale markings 96. An intermediate portion 95c of the needle is secured to the housing at a pivot point 98 so that the second end 95b of the needles moves with respect to the scale markings 96 in response to movement of the flexible member 92. The device can include an access port 99 that is penetrable by a needle to allow sampling of CSF.

In a further embodiment (not shown), a pressure measurement device is adapted for use with an external drainage system by a "Y" connector at the level of the patient's ventricles. The device can include one or more windows to enable a user to observe the position of the scale and position markings.

FIGS. 9–15 show another embodiment of an implantable pressure indicator device 100 in accordance with the present invention. The device 100 includes a housing 102 comprising a first housing 102a coupled to a second housing 102b. A sealing member 104, which seals a predetermined amount of fluid within first housing 102a, is disposed at the interface of the first and second housings 102a,b. The device 100 also includes an elongate member 108 that is axially movable with respect to the first and second housings 102a,b. The elongate member 108 preferably includes a position indicating member 110 that forms a scale in conjunction with a rod 112, as described below, to indicate the relative position of the elongate member with respect to the rod 112. The rod 112 is disposed within the second housing 102b and is substantially co-axial with the elongate member 108.

The first housing 102a has walls 116 extending from a closed end 118 to an open end 120 with an engaging mechanism 122 proximate the open end 120 for securing the first housing to the second housing 102b. The engaging mechanism 122 can be screw threads, an ultrasonic weld, an adhesive, or other means known to one of ordinary skill in the art. In one embodiment, the engaging mechanism comprises male threads.

The elongate member 108 includes a first end 108a and a second end 108b with a bore 114 formed in the first end 108a. The bore 114 can extend for the entire length of the elongate member 108 so that the elongate member is a hollow shaft, or the bore can extend for only a portion of the length of member 108. The bore 114 captures the rod 112 as the elongate member 108 moves in the housing over the pressure range of the device.

An optional disk 124 can be affixed to the second end 108b of the elongate member. The disk preferably has a diameter that is slightly less than the inner diameter of the first housing 102a. The disk 124 is useful to prevent or restrict any non-axial movement of the elongate member 108 within the first housing 102a. The disk 124 also helps to seal the second end 108b of the elongate member where the elongate member is a hollow shaft. The disk 124 can include a blind hole into which the second end 108b of the elongate member can be affixed.

The position indicating member 110 includes an axial opening 110a into which the first end 108a of the elongate member is inserted. The position indicating member 110 moves in concert with the elongate member 108 as elongate member 108 moves relative to the rod 112. The location of the position indicating member 110 in relation to the rod 112 indicates the differential between the external pressure and the pressure on the fluid 106 in the first housing 102a at the time of manufacture. The pressure differential manifests itself as the volume of the fluid in the first housing 102a, from which a physiological pressure is ultimately determined, as described below.

Figure 12:
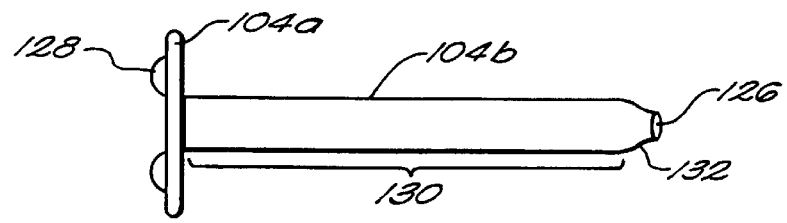
FIG. 12 is a side view of a sealing member which forms a portion of the pressure indicator of FIG. 9.
Figure 13:
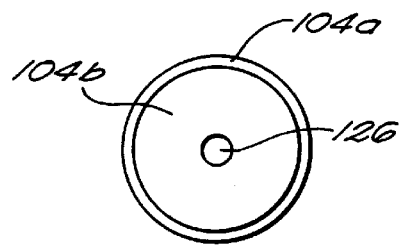
FIG. 13 is a front view of the sealing member of FIG. 12.

As shown in FIGS. 12–13, the sealing member 104 includes an O-ring 104a and an elongated, integral sleeve 104b extending from the O-ring and terminating in an aperture 126. The O-ring 104a has an inner and outer diameter that substantially correspond to the inner and outer diameter of the open end 120 of the first housing. Upon mating the open end 120 of the first housing 102a to the second housing 102b, the O-ring 104a forms a seal at the interface of the first and second housings.

The sleeve 104b has a tapered first portion 128 that extends from the O-ring and a second portion 130 that extends from the first portion. The second portion 130 has a substantially constant diameter and extends for a majority of the total length of the sealing member 104. A third portion 132 of the sleeve extends from the second portion 130 and tapers to a diameter that substantially matches a diameter of the elongate member 108 proximate the first end. The third portion 132 terminates in the aperture 126.

The first end 108a of the elongate member extends through the aperture 126 in the sealing member. The elongate member 108 is secured to the sealing member about the aperture 126 to form a seal between the sealing member 104 and the elongate member 108. The sealing member 104 and the elongate member 108 cooperate to seal the fluid 106 in the first housing 102a.

The second housing has an inlet end 138 and a mating end 136 with a shoulder 140 which increases the diameter of the mating end to receive the open end 120 of the first housing. As the first and second housings 102a,b are engaged, the shoulder 140 compresses the O-ring 104a to form a seal at the interface of the first and second housings and trap the fluid 106 in the first housing 102a. An engagement mechanism 142, such as screw threads or other means, disposed on the mating end 136 proximate the shoulder 140 couples the first and second housings 102a,b together.

The inlet end 138 of the second housing can include one or more passageways to communicate a pressure external to the device to the sealing member 104. In an exemplary embodiment, the inlet end 138 includes a first passageway 146 and a second passageway 148.

At least one scale marking 150 is located on the rod 112 and at least one position marking 152 is disposed on the position indicating member 110. The scale and position markings 150,152 form a scale to determine the location of the position indicating member 110 in the second housing 102b. The relative location of the position indicating member 110 indicates the volume of the fluid 106 in the first housing which is used to determine a physiological pressure, as discussed below.

The scale and position markings 150,152 can be formed from various materials that are discernible, i.e., at least partially opaque, to an imaging system, such as an X-ray, fluoroscope, ultrasound, computed axial tomography (CAT) scan, magnetic resonance imaging (MRI) system, position emission (PET) or other such system. It is understood that the rod 112 and position indicating member 110 can also be formed from such materials and may include apertures or other negative surface features that can be seen on a compatible imaging system. Exemplary materials for the scale and position markings 22,38 include radiopaque metals such as titanium, titanium alloys, stainless steel, boron, tantalum, cobalt chrome alloys, gadolinium, barium, and radiopaque materials such as barium sulfate, doped methylmethacrylate, zirconium dioxide, alumina, hydroxyapatite, and processed bone.

The scale and position markings 150,152 can be formed in many geometric configurations. The markings can be wires and/or apertures that are substantially coplanar, as well as circumferential markings or grooves. Such an arrangement can reduce parallax and allow the markings to be seen from a wide range of angles. It is understood that one of ordinary skill in the art can readily modify the particular embodiments disclosed herein.

Figure 14:
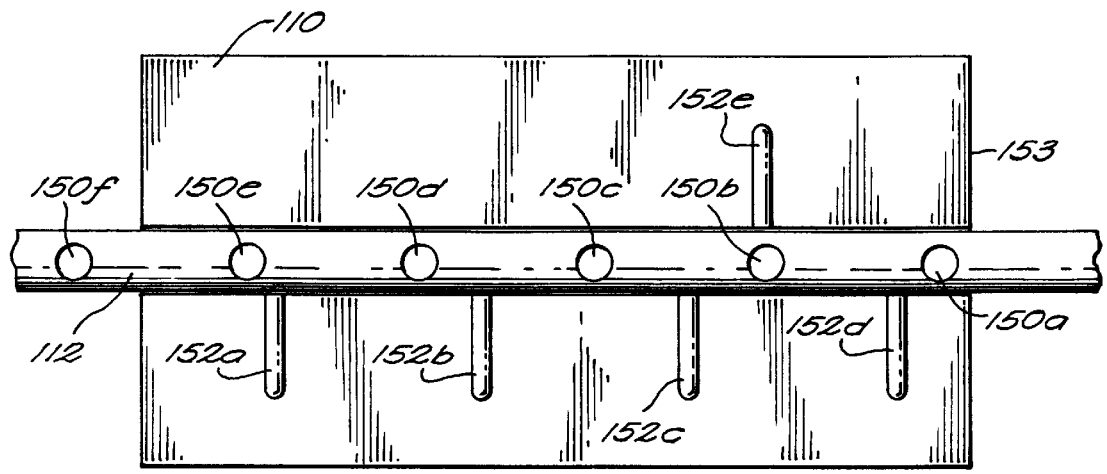
FIG. 14 is a detailed cross sectional view of a position indicating member, which forms a portion of the pressure indicator of FIG. 9, shown in a first position.
Figure 15:
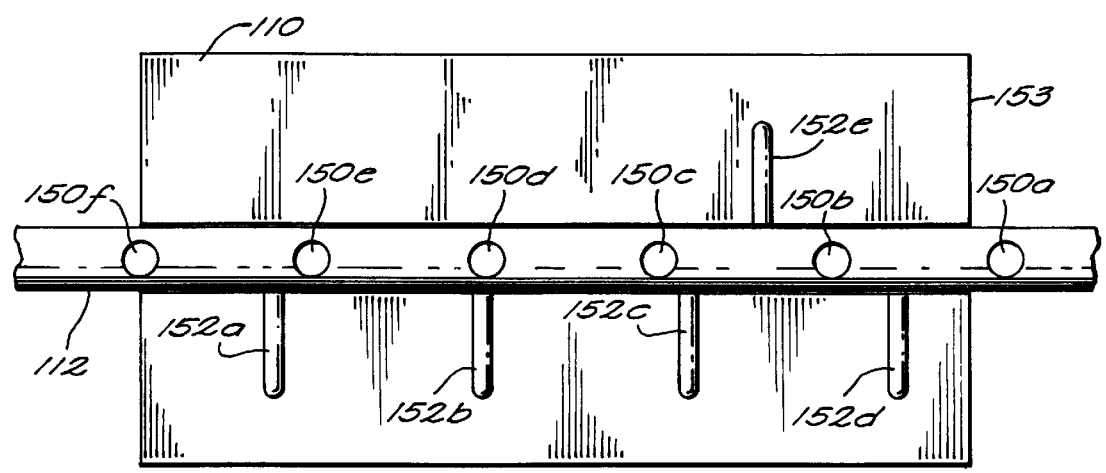
FIG. 15 is a detailed cross sectional view of the position indicating member of FIG. 14 shown in second position.

FIGS. 14–15 show an illustrative embodiment of a scale formed from the scale and position markings 150,152. The scale markings 150 comprise apertures 150a–f formed in a metal (e.g., titanium) rod 112 and spaced at about 1.0 millimeter increments. The position markings 152 include a single metal (e.g., titanium) wire 152e above the rod 112 and four metal (e.g., titanium) wires 152a–d below the rod. It is understood that the terms "above" and "below" are relative terms only and correspond to the exemplary embodiment shown.

The single metal wire 152e is inserted into a hole in the position indicating 110 member with an interference fit. The four metal wires 152a–d are similarly inserted into an opposite side of the position indicating member.

The four wires 152a–d are spaced approximately at 1.2 millimeter intervals along the length of the position indicating member 110, with the wire 152d nearest the inlet end of the second housing being about 0.4 millimeter from an end 153 of the position indicating member 110. The single wire 152e is about 1.2 millimeters from the end 153 of the position indicating member. Thus, the single wire 152e is not directly aligned with any of the four wires 152a–d.

FIG. 14 shows a respective aperture 150b aligned with the single wire 152b. In this case, the location of the position indicating member 110 with respect to the rod 112 is readily determined. From this positional arrangement, the fluid 28 volume and corresponding external pressure are known. As discussed below, the physiological pressure proximate a site of implantation can then be determined in relation to ambient pressure.

FIG. 15 shows the single wire 152e not aligned with an aperture 150. Instead, it is disposed between apertures 150c and 150b. Thus, the single wire 152e does not provide the exact location of the position indicating member 110 with respect to the rod 112. However, the third wire 152d is aligned with an aperture 150d. Since, in the exemplary embodiment, the spacing of the apertures 150 is known to be 1.0 millimeter and the spacing of the four wires 152a–d is known to be 1.2 millimeters, the exact location of the position indicating member 110 in relation to the rod 112 can be readily determined. From the location of the position indicating member 110 with respect to the rod 112, a physiological pressure can be established, as discussed below.

The shape and dimensions of the various components described above can vary depending upon the intended application, the anticipated site of implantation, and the expected pressure ranges. The components are sized to allow free movement of the elongate member within the first and second housings. The sealing member can flex to accommodate movement of the elongate member and/or it can elastically deform as the fluid in the first housing expands. Moreover, movement of the elongate member in response to pressure changes need not be linear, but it should be predictable.

The housing 102 can be of any shape that allows sufficient axial movement of the elongate member 108 over a pressure range of the device. The housing can be formed in any suitable shape, including annular, cylindrical, ovular, and rectangular. In a preferred embodiment, the housing has a cylindrical shape.

In an exemplary embodiment of the device, the first housing 102a is about 18.50 millimeters in length and has inner and outer diameters o about 4.00 and 5.00 millimeters, respectively. The elongate member 108 is about 23.5 millimeters in length with a 1.13 millimeter outer diameter and 0.80 millimeter bore diameter. The O-ring 104a of the sealing member has inner and outer diameters that correspond to the inner and outer diameters of the first housing and has an overall length of about 20.00 millimeters. The sleeve 104b second portion has a diameter of about 1.25 millimeters apering to the aperture 126 which has a diameter of about 1.13 millimeters to match the outer diameter of the elongate member 108. Generally, the thickness of the sleeve 104b is lesthan about 0.30 millimeter. The position indicating member 110 has a length of about 4.40 millimeters and a diameter of about 3.80 millimeters. The holes for the wires 152 are about 0.40 millimeters in diameter and about 1.20 millimeters in depth. The rod 112 is about 20.50 millimeters in length and 0.60 millimeter in diameter. The second housing 102b has an inner diameter of about 4.00 millimeters and outer diameters of about 5.00 millimeters at the inlet end and about 7.00 millimeters at the mating end.

It is understood that the above dimensions are illustrative and can be readily modified by one of ordinary skill in the art.

In operation, the fluid 106 in the first housing 102a expands and contracts until the pressure on the fluid 106 and the external pressure are substantially equal. This causes the elongate member 108 and position indicating member 110 to move with respect to the rod 112. The location of the position indicating member 110 is representative of a volume of the fluid 106 in the first housing 102a. From the volume of the fluid 106, the corresponding external pressure is determined. Ambient pressure is established and subtracted from the external pressure to determine a pressure at the site of implantation.

FIG. 9 shows the maximum pressure measurable by the device. The pressure differential on the opposite sides of the sealing member 104 causes the second end 108b of the elongate member move to abut the sealed end 118 of the first housing.

FIG. 10 shows the minimum pressure that is measurable by the device. As the pressure differential decreases, the fluid expands thereby moving the elongate member in the direction of the second housing 102b.

To determine the pressure at the site of implantation, or shunt system pressure, an image of the device must be obtained. This image can be obtained using a suitable imaging system, as noted above. Examples of such systems include X-ray, fluoroscope, ultrasound, computer axial tomography (CAT) scan, and magnetic resonance imaging (MRI) systems and position emission (PET) scans. The image indicates the relative position of the position indicating member 110 with respect to the rod 112. That is, the imaging system reveals the location of the position indicating member 110 in relation to the scale and position markings 150,152. The location of the position indicating member 110 is compared with a known initial position of the position indicating member to determine whether the external pressure has increased or decreased.

The pressure measurement device of the present invention has a range of measurable pressures that is appropriate for a particular application. For example, intracranial pressure is generally measured in millimeters of water (mm $H_2O$)with a typical range from about 0 to 200 mm $H_2$) above ambient pressure. Pathological levels of intracranial pressure above about 250 mm $H_2O$ are generally considered dangerous. A pressure measurement device for implantation within the cranium of a patient should therefore be able to measure pressures within this range, preferably with a resolution of about 10 to 20 mm $H_2O$ or better.

It is desirable for an implanted device to be able to measure intracranial pressure at low ambient pressures in conjunction with a nominal intracranial pressure and at high ambient pressures with elevated intracranial pressures. A typical atmospheric pressure is about 10400 mm $H_2O$ (one standard atmosphere is about 10332 mm $H_2O$). In an exemplary embodiment, the device is assembled at an ambient pressure at about 10400 mm $H_2O$ and has a measurable pressure range from about 10250 to about 10850 mm $H_2O$. Thus, the device can measure a pressure from about 150 mm $H_2O$ below to about 450 mm $H_2O$ above an atmospheric pressure of about 10400 mm $H_2O$.

In the exemplary embodiment, the resolution of the device is about 10 mm $H_2O$ in the range from 10250 mm $H_2O$ to about 10850 mm $H_2O$ where the initial pressure on the fluid in the first housing is about 10400 mm $H_2O$. Thus, movement of the elongate member by about 10 millimeters is detectable in the exemplary embodiment. A movement of about 1 millimeter results from about a 50 mm $H_2O$ change in pressure differential.

It is understood that the device 100 can be adapted for implantation by itself or for connection to a shunt system as described in conjunction with the embodiment of FIG. 1. In a stand-alone application, the first passageway 146 can be covered with a membrane and the second passageway blocked or sealed. Further, surgical tubing extending from the first passageway can communicate with a sealed membrane to allow the device to measure pressure proximate the membrane. Thus, the housing can be implanted under the scalp and the membrane be located within the cranium. For coupling to a shunt system, tubing can coupled to the first and second passageways 146,148. The first passageway can serve as an inlet and the second passageway as an outlet for fluid through the shunt system.

In addition to intracranial pressure measurements, the pressure measurement device of the present invention can readily be adapted for other applications as well. For example, the device can be incorporated into a vascular aneurysm repair sheath to measure blood pressure. In another embodiment, a pressure measurement device in placed within the gastrointestinal tract to measure physiological pressures proximate the device. It is understood that other such applications will be readily apparent to one of ordinary skill in the art.

The components of the device can be made from a variety of biocompatible materials having the properties required for the particular component. For example, the first housing is formed from a suitably rigid bioimplantable material. The first housing must be sufficiently rigid so that the housing does not deform in the presence of a physiological pressure to be measured. Exemplary materials include polyethylene. A preferred material is polyethersulphone.

The disk 124 can be made from a variety of materials suitable for implantation within the body. Exemplary materials include polymethymethacrylate, polyurethane, or a medical grade silicone. A preferred material is a high-durometer silicone.

The sealing member 104 is formed from a bioimplantable material of sufficient flexibility to allow movement of the elongate member 108 with minimal resistance. The material must be flexible and can also be elastic. Preferably, the material can withstand pressures beyond the range measurable by the device, such as those pressures experienced at high altitudes or at depths below sea level. The sealing member material should not adhere to itself or other device components. Exemplary materials include polymers such as silicones and polyurethanes. A preferred material for the sealing member is a medical grade silicone unpregnated with polytetrafluoroethylene (PTFE).

The rod 112 can be formed from suitable rigid, bioimplantable materials in which markings can be formed that are discernible on an imaging system, such as X-ray, fluoroscope, or magnetic resonance imaging system. Suitable materials include polymers and metals such as titanium, titanium alloys, stainless steel and polymers. A preferred material is titanium.

The fluid 106 sealed in the first housing 102a can any fluid that adequately expands and contracts in response to pressure. Suitable fluids includes air, nitrogen, and noble gases such as argon. Chlorofluorocarbons (CFCs) can also be used in conjunction with an infusion pump. A preferred fluid is air.

One skilled in that art will realize further features and advantages of the invention from the above-described embodiments. Accordingly, the invention is not to be limited by what has been particularly shown and described, except as indicated by the appended claims. All references cited herein are expressly incorporated by reference in their entirety.

What is claimed is:

1. An implantable pressure measurement device, comprising:

a housing having a passageway, a chamber, and at least one scale marking, the passageway being effective to communicate a pressure that is external to the device into the chamber;

a flexible member disposed in the chamber, the flexible member containing a fluid at a predetermined pressure; and a position indicating member coupled to the flexible member and including at least one position marking, the position indicating member being movable within the passageway such that the relative position of the position indicating member with respect to the housing is externally imageable and is indicative of a pressure differential between the pressure external to the device and ambient pressure.

2. The device according to claim 1, wherein the at least one position marking and the at least one scale marking are at least partially opaque and detectable by an imaging system.

3. The device according to claim 1, wherein the at least one scale marking includes a plurality of markings of varying opacity and with varying levels of detectability by an external imaging system.

4. The device according to claim 1, wherein the at least one position marking and the at least one scale marking form a Vernier scale.

5. The device according to claim 1, wherein the at least one position marking and the at least one scale marking are substantially planar.

6. The device according to claim 1, further comprising a covering member effective to isolate the device from bodily fluids.

7. The device according to claim 6, further comprising a second fluid enclosed by the covering member.

8. The device according to claim 1, wherein the device is adapted for coupling to a shunt valve system.

9. The device according to claim 1, wherein the flexible member includes a bellows portion.

10. The device according to claim 1, wherein the fluid is selected from the group consisting of air, oxygen, and nitrogen.

11. The device according to claim 1, wherein the at least one position marking and the at least one scale marking are made from a radiopaque material.

12. The device according to claim 1, wherein the at least one position marking comprises a needle in pivotal communication with the flexible member.

* * * * *